US012558066B2

(12) United States Patent
De Beni

(10) Patent No.: US 12,558,066 B2
(45) Date of Patent: Feb. 24, 2026

(54) SYSTEM AND METHOD FOR ACQUIRING DIAGNOSTIC IMAGES BY ULTRASOUNDS

(71) Applicant: Esaote S.p.A., Genoa (IT)

(72) Inventor: Stefano De Beni, Genoa (IT)

(73) Assignee: Esaote S.p.A., Genoa (IT)

( * ) Notice: Subject to any disclaimer, the term of this patent is extended or adjusted under 35 U.S.C. 154(b) by 43 days.

(21) Appl. No.: 18/407,510

(22) Filed: Jan. 9, 2024

(65) Prior Publication Data

US 2024/0237968 A1 Jul. 18, 2024

(30) Foreign Application Priority Data

Jan. 17, 2023 (EP) ..................................... 23151919

(51) Int. Cl.
*A61B 8/00* (2006.01)

(52) U.S. Cl.
CPC .......... *A61B 8/4494* (2013.01); *A61B 8/4254* (2013.01); *A61B 8/4405* (2013.01); *A61B 8/4433* (2013.01); *A61B 8/565* (2013.01)

(58) Field of Classification Search
CPC ................ A61B 8/4494; A61B 8/4254; A61B 8/4405; A61B 8/4433; A61B 8/565; A61B 8/4245; A61B 8/5207; A61B 8/5246; A61B 8/56
See application file for complete search history.

(56) References Cited

U.S. PATENT DOCUMENTS

| | | | | |
|---|---|---|---|---|
| 2006/0247520 | A1* | 11/2006 | McGee ................. | A61B 34/20 |
| | | | | 600/434 |
| 2019/0090846 | A1* | 3/2019 | Lee ...................... | A61B 8/4405 |
| 2020/0245973 | A1* | 8/2020 | Cox ..................... | A61B 8/0891 |

(Continued)

FOREIGN PATENT DOCUMENTS

| | | |
|---|---|---|
| EP | 1467317 A1 | 10/2004 |
| EP | 2404551 A1 | 1/2012 |

(Continued)

OTHER PUBLICATIONS

European Search Report and Written Opinion dated Jun. 29, 2023, which issued in the corresponding European Patent Application No. EP 23 15 1919.

*Primary Examiner* — Alexei Bykhovski
(74) *Attorney, Agent, or Firm* — Dickinson Wright PLLC

(57) ABSTRACT

A system for acquiring ultrasound diagnostic images is provided that has an ultrasound imaging device and a probe tracking system. The ultrasound imaging device has: a probe provided with one or more electroacoustic transducers; a unit transmitting an ultrasonic beam through the transducers within a body under examination; and a unit receiving and processing ultrasound signals received from the transducers for generating real-time images. The a probe tracking system has probe detecting sensors and a processing unit for calculating the probe position and/or the probe orientation and/or the probe displacement from the data provided by the probe detecting sensors At least the processing unit of the probe tracking unit is a physically separated unit from the ultrasound imaging device and said ultrasound imaging device and said probe tracking system communicate by means of a short-range wireless communication protocol being provided respectively with a corresponding transmitting and/or receiving communication unit.

10 Claims, 4 Drawing Sheets

(56)     References Cited

U.S. PATENT DOCUMENTS

2021/0322148  A1     10/2021  Mitra et al.
2022/0240896  A1 *    8/2022  Meurer ................ A61B 8/4427

FOREIGN PATENT DOCUMENTS

EP           2998932  A1 *   3/2016   ........... G06T 11/003
EP           3689247  A1     8/2020
EP         4 088 664  A1    11/2022

* cited by examiner

SYSTEM AND METHOD FOR ACQUIRING DIAGNOSTIC IMAGES BY ULTRASOUNDS

BACKGROUND

The present disclosure relates to systems and methods for acquiring ultrasound images in combination with a probe tracking system.

Ultrasound probe tracking is a technique which is known and widely used in the art for carrying out several kinds of imaging. Probe tracking is used, for example, in order to collect three-dimensional images of a target body. In this case, series of ultrasound images of a target body are acquired along adjacent slices. The probe is translated transversally or rotated transversally to the plane along which the image is acquired at the current position and orientation of the probe. Images are acquired at different probe positions, said images corresponding to a sequence of adjacent slices having a predetermined distance one from the other. By tracking the probe position and/or orientation and/or the displacement of the probe from the position between two following image acquisitions at each of two adjacent slices, a geometric relation between the images related to each slice can be determined and a volumetric (three-dimensional image) of the target body can be reconstructed by combining said images along the sequence of adjacent slices.

A further application in which probe tracking is currently used relates to techniques for combining or fusing images obtained in imaging sessions carried out at different times and/or with different imaging techniques. This kind of multimodality image fusion techniques may be provided, for example, for the monitoring of an anatomical region during insertion of metallic objects, or objects made at least partly of metal, inside the imaging region, which metallic objects disturb standard tracking systems. Alternatively, this kind of multimodal images fusion techniques are used to combine high resolution three-dimensional images acquired at a previous time with real time images of the same target body.

In relation to the first case, document EP1467317A1 discloses a method and an apparatus for combining first and second image data of an object, according to which an ultrasound detector repeatedly generates the first image data of the object while the second image data of the object are generated separately by means of a CT an MR, a PET or an x-ray apparatus. The second image data are three-dimensional image data of the object. A combination device combines the first and second image data. A tracker of the ultrasound probe is provided for tracking the position of the ultrasound probe and of the two-dimensional data generated by the ultrasound probe. The tracking device is used as a reference coordinate system in relation to which first and second image data can be registered for image fusion. A certain position of the ultrasound probe, and thus of the slice or section plane along which the image data is collected, can be thus related to an identical section plane or slice in the three-dimensional image data allowing reconstruction of the image along said slice or section plane by using the second image data instead of the first image data generated by the ultrasound probe.

Document EP2404551A1 discloses an imaging method for operating an imaging device for the monitoring of an anatomical region during insertion of metallic objects or objects made at least partly of metal inside said region, which metallic objects disturb standard tracking systems, wherein the device comprises at least a first three-dimensional diagnostic image acquisition scanner and at least an ultrasound system as a second two-dimensional image acquisition scanner, at least a storage unit for storing image data acquired by said first image acquisition scanner and by said second acquisition scanner, at least a registration and processing unit which acquires two-dimensional images and associates them to three-dimensional images, at least a tracking system for determining the displacement and/or position and/or orientation in space of said second two-dimensional diagnostic image acquisition scanner, at least a display unit, and in which device the second image acquisition scanner comprises a probe and a control processing unit for driving the probe to emit ultrasound beams and to receive reflected echoes and for generating images from said reflected echoes, wherein said method for operating the imaging device comprises the following steps:

a) acquiring a three-dimensional image of a specific anatomical district of a target body under examination for example by a computed axial tomography device and storing said image data;

b) finding at least a reference point within said anatomical district;

c) acquiring a two-dimensional image along or at a first section slice or plane of said anatomical district passing by said at least one reference point by means of the said secondo imaging scanner, i.e., said ultrasound probe;

d) identifying said first section plane or slice of the acquired two-dimensional image, within the stored three-dimensional image;

e) constructing a two-dimensional image with data of the three-dimensional image falling along said first section slice or plane which has been identified and corresponding to that of the acquired two-dimensional image;

f) moving said ultrasound probe towards at least a further section slice or plane of said anatomical district having a position and/or orientation different than that of said first section slice or plane of step b);

g) tracking the displacement of said ultrasound probe for obtaining the image at said further section slice or plane;

h) identifying said further section slice or plane within the stored three-dimensional image by using data related to the tracking of the displacement of said ultrasound probe;

i) constructing a two-dimensional image with data of the three-dimensional image falling along said further section slice or plane identified at step h);

displaying a combined image deriving from the combination of the two-dimensional image which has been reconstructed from the three-dimensional data with the two-dimensional echographic image, the contribution of the two-dimensional image reconstructed from the three-dimensional data corresponds to the representation of the anatomical structure and the contribution of the echographic image corresponds at least to the representation of the metallic object.

Document EP2998932A1 discloses a further example in which probe tracking is carried out. Also this document discloses a method and a system for the fusion of ultrasound images acquired in real time with pre-acquired images of the same target body. An embodiment of the disclosed method comprises the following steps:

a) acquisition of a first 3D ultrasound image in real-time, said 3D acquisition being performed such to obtain both morphological information (imaging part) and Doppler information;

b) identification of at least one known reference pattern or object within the pre-acquired 3D image and the 3D ultrasound image;

c) registration of the 3D ultrasound image acquired in real-time with the pre-acquired 3D image by using the reference pattern or object;

d) fusion of the 3D ultrasound images of a sequence of 3D ultrasound images acquired in real-time with the pre-acquired 3D image by using data of the co-registration between said first 3D ultrasound image and the pre-acquired 3D image;

e) display of fusion tomographic images, each fusion image comprising the corresponding ultrasound image acquired in real-time and the pre-acquired image.

In order to carry out the disclosed method, EP2998932 discloses also a device for acquiring and displaying ultrasound images, comprising:

a probe provided with one or more electroacoustic transducers, a unit transmitting an ultrasonic beam through the transducers within a body under examination, a unit receiving and processing ultrasound signals received from the transducers for generating real-time images, a probe tracking system, and a tracking processing unit for calculating the probe position and/or orientation and/or displacement in a reference system and for the registration of an acquired real-time ultrasound image with a pre-acquired image, combining the coordinate system of the body under examination, the coordinate system of the probe and the coordinate system of the pre-acquired image into a single coordinate system, and a display for displaying a sequence of fusion images, each fusion image comprising the corresponding real-time image and the pre-acquired image, where the registration means operate in real-time for each or some real-time images.

A further example is disclosed in EP3689247A1. In this document a system and a method are disclosed which provide for combination and/or fusion of a representation of an external or envelope surface of a target body with an image of the structure of the said target body inside the said envelope surface and/or below the said external surface. The disclosed method comprises the steps of providing a digital representation of the shape of a surface or boundary of an anatomic region or organ; acquiring an ultrasound image by ultrasound scanning the anatomic region or organ; and combining the digital representation of the shape of the surface or boundary of the anatomic region or organ by registering the digital representation of the shape of the surface or boundary and the ultrasound image as a function of the difference in position of selected reference points on the digital representation of the surface or boundary and on the ultrasound image, the position of the reference points on the ultrasound image being determined by tracking the probe position at the reference points at the anatomic region or organ of a real body and in a spatial reference system, in which the anatomic region or the organ of the real body is placed.

Tracking systems are common in the field of ultrasound imaging and are configured according to different techniques. Tracking of the probe may be carried out by optical means such as a camera in combination with image processing tools and markers from which the probe position, the probe orientation and the probe displacement, and also the reference system in which the probe is placed, are defined. In an alternative solution, probe tracking is carried out by magnetic means that detect perturbations induced on a magnetic field by change in position and/or orientation and/or displacement. Other tracking systems are known in addition to the two examples cited. A description of the different probe tracking techniques can be found in "A review of calibration techniques for freehand 3-D ultrasound systems", Laurence Mercier, Thomas Langø, Frank Lindseth, Louis D Collins, Ultrasound Med Biol 2005 February; 31(2): 143-65, doi: 10.1016/j.ultrasmedbio.2004.11.001.

In general, a tracking system of any kind comprises sensors and/or markers and/or active or passive tags associated to the probe and a detector in a predefined reference coordinate system describing the space in which the probe is placed and is displaced. A tracking data processing unit receives the signals from said sensors and/or markers and/or active or passive tags collected by said detector and calculates the position of the probe and/or the orientation of the probe and/or the displacement path of the probe, as well as, optionally, additional displacement parameters such as linear and/or rotational acceleration and speed. In some solutions also the target body position and/or orientation and/or displacement within the reference coordinate system defined by the tracking system is determined. This can be done also by the provision on the target body of similar sensors and/or markers and/or active or passive tags as the ones associated to the probe.

According to the state of the art, the hardware and the related software, for example the one described above, are integrated in the ultrasound system. This introduces high additional costs for the ultrasound system and also require that each ultrasound system provided with the tracking system needs to be subjected to certification.

Furthermore, providing the ultrasound system with an integrated tracking system for the probe need to follow design constraints of the ultrasound system itself.

The hardware of the ultrasound system and the one of the tracking systems might have different technical trends of development, so that in some cases it may happen that one of the tracking system or the ultrasound system is still in commerce while the other is not anymore up to date.

Therefore, there is the need to provide for a different configuration of the combination of ultrasound systems and probe and/or patient tracking systems which allows for overcoming the drawbacks of the current integrated configuration of the tracking system in the ultrasound imaging system.

SUMMARY OF THE INVENTION

According to a first embodiment, a system for acquiring ultrasound diagnostic images, comprises:

an ultrasound imaging device comprising:

a probe provided with one or more electroacoustic transducers;

a unit transmitting an ultrasonic beam through the transducers within a body under examination;

a unit receiving and processing ultrasound signals received from the transducers for generating real-time images;

a probe tracking system comprising detecting sensor of the probe and a processing unit for calculating the probe position and/or the probe orientation and/or the probe displacement from the data provided by the probe detecting sensors, wherein at least the processing unit of the probe tracking unit is a physically separated unit from the ultrasound imaging device and said ultrasound imaging device and said probe tracking system communicates by means of a short-range wireless communication protocol being provided respectively with a corresponding transmitting and/or receiving communication unit.

According to an embodiment, said short range communication protocols can be selected from the following list: Bluetooth, Wi-Fi, ZigBee, UWB, IR.

According to a further possible feature, the system further comprises a cart provided stably with the probe tracking system.

The cart may be further provided with a support for the ultrasound imaging device, the said support and the said ultrasound imaging device being provided with cooperating releasable mutual fastening means.

Separately from the said mutual fastening means and/or integrated in at least one or some of the said mutual fastening means of the ultrasound device to the support on the cart, there might be provided electric connectors for connecting at least one port of the ultrasound imaging device with a power source.

Alternatively or in combination, the ultrasound imaging device may be provided with other ports, such as a RX/TX port of a communication interface to be connected with a wired connection by means of the said connectors to a communication network, for example a communication network operating according to a known network protocol, such as for example a TCP/IP protocol or other.

Still according to a further possible embodiment, the ultrasound device may be also provided with a video port which can be connected to at least one display provided stably on the cart.

All the above disclosed connectors on the support of the cart and corresponding connectors and/or ports of the ultrasound device can be configured in such a way that the electric connection is automatically generated when the ultrasound imaging device is secured to the support and is automatically cut when the ultrasound imaging device is disengaged and/or separated from the support on the cart.

In an embodiment, an image processing unit may be provided for image fusion to combine image data of an image acquired in real time by the probe with the image data along the same slice or volume of an image which has been acquired at an earlier time and/or with a different imaging technique, such as a CT, MRI, PET or other imaging techniques.

The image fusion processing unit may be provided with a memory for storing the earlier acquired digital image data. Furthermore, the image fusion processing unit may also be provided with a registration unit for registering within a common coordinate system the previously acquired image and the image acquired in real time by the ultrasound imaging device.

According to still another feature, the generic processing hardware may have stored in a memory a software program coding the instructions for making said generic processor able to carry out the functions according to one or more of the methods and systems disclosed in EP2404551A1 and/or in EP3689247 and/or EP2998932, which descriptions are to be considered part of the present disclosure.

According to a specific embodiment, the tracking system comprises:

elements for registering an ultrasound image acquired real-time by the ultrasound imaging device with a pre-acquired image and for registering the coordinate system of the body under examination, the coordinate system of the probe and the coordinate system of the pre-acquired image into a single coordinate system, and elements for displaying a sequence of fusion images, each fusion image comprising the corresponding real-time image and the image data of pre-acquired image falling onto the same field of view and/or sector volume and/or slice of the image acquired by the ultrasound image device.

The present disclosure relates also to a method for acquiring target body, comprising:

tracking the probe position and/or orientation and/or displacement during image acquisition by means of said probe;

univocally associating the probe position and/or the probe orientation and/or the probe displacement to an image acquired with said probe in said position and/or orientation and/or during said displacement;

storing said combination of acquired image and data on the position and/or orientation and/or displacement of the probe during acquisition of said image;

wherein the tracking the univocal association of position and/or orientation and/or displacement of the probe and storing in a memory are carried out by means of a tracking system which is a separate physical unit from the ultrasound device, while the ultrasound device and said separate physical unit communicate by means of a short-range wireless communication protocol and/or a normal wireless communication protocol and the ultrasound imaging device can be removably secured to a common support structure of the said tracking system and the said ultrasound imaging device, such as a cart or a stand.

DETAILED DESCRIPTION OF THE DRAWINGS

Figure 1:
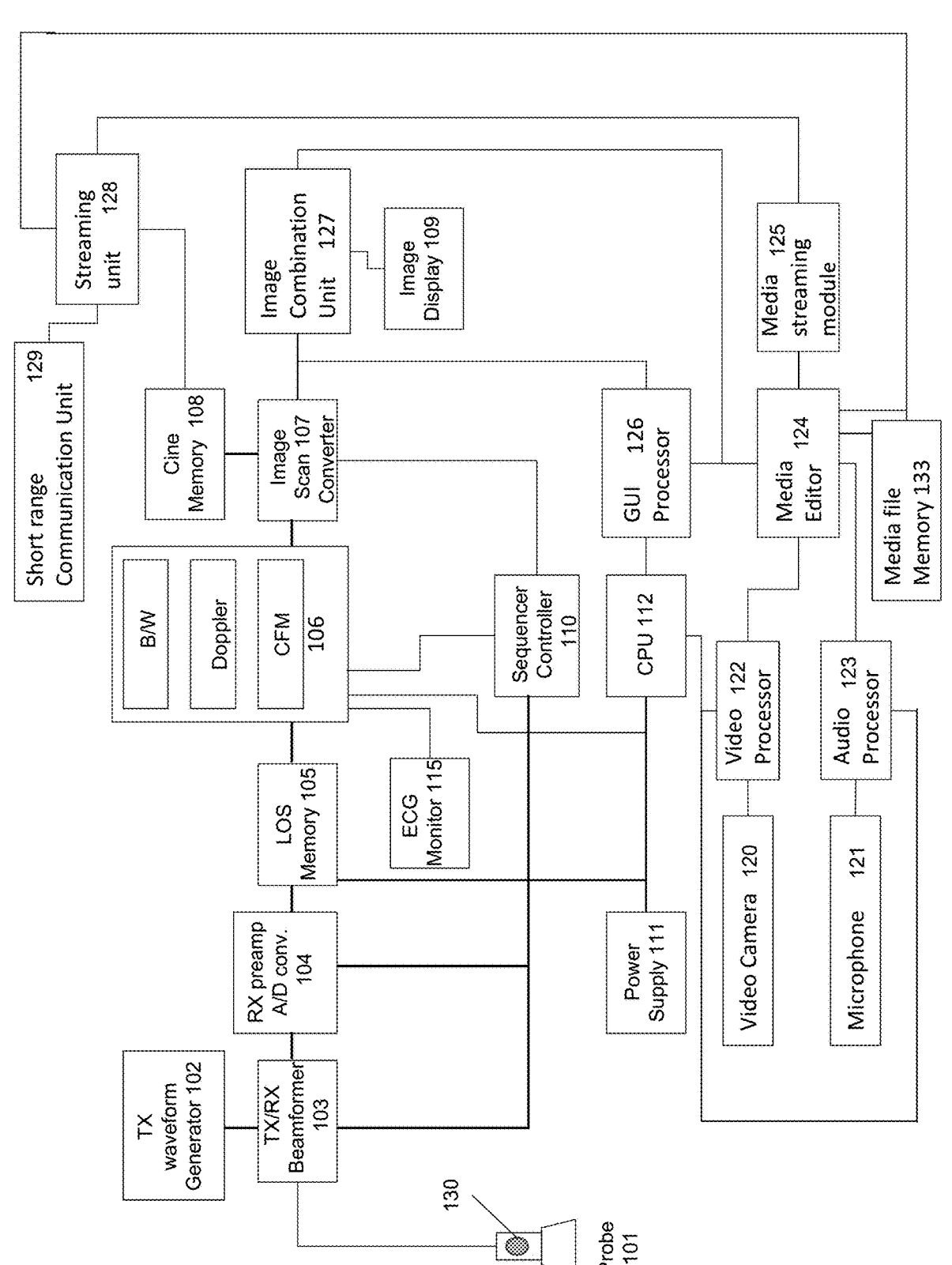
FIG. 1 shows a high-level diagram of an ultrasound system as an example of a medical diagnostic device.

FIG. 1 illustrates a high-level block diagram of an ultrasound system which is capable of providing the features according to embodiments herein. Portions of the system (as defined by various functional blocks) may be implemented with dedicated hardware, such as transmit/receive (TX/RX) driving/preamp and power switching circuitry, which may utilize analog components. Digital components, DSPs and/or FPGAs, may be utilized to implement the sequencer controller and the timing generator.

The ultrasound system of FIG. 1 includes one or more ultrasound probes 101. The probe 101 may include various transducer array configurations, such as a one-dimensional array, a two-dimensional array, a linear array, a convex array and the like. The transducers of the array may be managed to operate as a 1D array, 1.25D array, 1.5D array, 1.75D array, 2D array, 3D array, 4D array, etc.

The ultrasound probe 101 is coupled over a wired or wireless link to a beamformer 103. The beamformer 103 includes a transmit (TX) beamformer and a receive (RX) beamformer that are jointly represented by TX/RX beamformer 103. The beamformer 103 supplies transmit signals to the probe 101 and performs beamforming of "echo" signals that are received by the probe 101.

A TX waveform generator 102 is coupled to the beamformer 103 and generates the transmit signals that are supplied from the beamformer 103 to the probe 101. The transmit signals may represent various types of ultrasound TX signals such as used in connection with B-mode imaging, color Doppler imaging, pulse-inversion transmit techniques, contrast-based imaging, M-mode imaging and the like. The beamformer 103 performs beamforming upon received echo signals to form beamformed echo signals in connection pixel locations distributed across the region of interest. For example, in accordance with certain embodiments, the transducer elements generate raw analog receive signals that are supplied to the beamformer. The beamformer adjusts the delays to focus the receive signal along a select receive beam and at a select depth within the ROI. The beamformer adjusts the weighting of the receive signals to obtain a desired apodization and profile. The beamformer sums the delayed, weighted receive signals to form RF beamformed signals. The RF beamformed signals are digitized at a select sampling rate by the RX preamp and A/D converter 104. The RF beamformed signals are converted to I, Q data pairs.

The I, Q data pairs are saved as image pixels in the line of sight (LOS) memory. For example, the LOS memory may include LOS memory portions associated with each line of sight through the ROI. The I, Q data pairs, defining the image pixels for corresponding individual ROI locations along a corresponding LOS, are saved in the corresponding LOS memory portion. A collection of image pixels (e.g., I, Q data pairs) are collected over time and saved in the LOS memory 105. The image pixels correspond to tissue and other anatomy within the ROI.

In embodiments, a dedicated sequencer/timing controller 110 may be programmed to manage acquisition timing which can be generalized as a sequence of firings. The sequence controller 110 manages operation of the TX/RX beamformer 103 and the A/D converter 104.

One or more processors 106 various processing operations as described herein. The CPU 112 may perform control operations of various units such as the processors 106, the GUI-image processor 162, the video processor 122 and the sound or audio processor 123.

Among other things, the processor 106 and/or CPU 112 analyse the image pixels to determine differences between each following image from a preceding one of a time sequence of images and to control the video processors and/or the media editor or the streaming module 125 in order to discard from the data stream images which are identical or almost identical to the previous one by maintaining on screen the previous image.

The processor 106 and/or CPU 112 also performs conventional ultrasound operations. For example, the processor 106 executes a B/W module to generate B-mode images.

The processor 106 and/or CPU 112 executes a Doppler module to generate Doppler images. The processor executes a Colour flow module (CFM) to generate color flow images. The processor 106 and/or CPU 112 may implement additional ultrasound imaging and measurement operations. Optionally, the processor 106 and/or CPU 112 may filter the displacements to eliminate movement-related artifacts.

An image scan converter 107 performs scan conversion on the image pixels to convert the format of the image pixels from the coordinate system of the ultrasound acquisition signal path (e.g., the beamformer, etc.) and the coordinate system of the display. For example, the scan converter 107 may convert the image pixels from polar coordinates to Cartesian coordinates for image frames.

A cine memory 108 stores a collection of image frames over time. The image frames may be stored formatted in polar coordinates, Cartesian coordinates or another coordinate system.

An image display 109 displays various ultrasound information, such as the image frames and information measured in accordance with embodiments herein. The display 109 displays the ultrasound image with the region of interest shown. Optionally, the system of FIG. 1 may include an ECG monitor not shown that couples an ECG sensor to the patient and records an ECG signal indicative of the patient's heart rate. The processor 106 and/or sequence controller 110 synchronize the image acquisition steps with the ECG signal.

The blocks/modules illustrated in FIG. 1 can be implemented with dedicated hardware (DPSs, FPGAs, memories) and/or in software with one or more processors.

A control CPU module 112 is configured to perform various tasks such as implementing the user/interface and overall system configuration/control. In case of fully software implementation of the ultrasound signal path, the processing node usually hosts also the functions of the control CPU.

A power supply circuit 111 is provided to supply power to the various circuits, modules, processors, memory components, and the like. The power front-end may be an A.C. power source and/or a battery power source (e.g., in connection with portable operation).

According to a further feature an image combination unit 127 may be present in which the B-mode image data of at least of a region of interest and the corresponding graphic representation of the GUI and further textual information associated to the image acquisition such as data of the patient, indication of the diagnosis, setting of the scanner is combined for the superimposed display of the B-mode image and of said data.

The acquired images as well as the GUI images and the textual data are combined in the Image combination unit and the combined images are displayed on the image display of the ultrasound system.

The said acquired images and the GUI images and the textual data are also processed by a media editor 124. The media editor 124 is configured to combine the acquired images, the images of the GUI and the textual data as well as other imaged data such as acoustic data and further video images in order to generate a multimedia video clip coded as a multimedia file according to one or more of the current available coding protocols for video and acoustic files.

GUI processor 126 is also configured to generate a graphic code, such as a bar code or a QR code in which information can be coded such as an ID code of the ultrasound system and further other information as for example information to access streaming data from the image display screen 109. By reading the code a device can retrieve the information necessary to start a streaming connection with the ultrasound apparatus.

Acoustic data may be generated by the ultrasound system such as the audio files representing the hematic flows in the various flow imaging modes such as Doppler, power Doppler, etc. According to a variant shown in FIG. 1, the acoustic data can be generated by a microphone 121 capturing noises or speeches held by one or more of the operators using the ultrasound system. Microphone signals are fed to an audio processor 123 which is configured to code the acoustic signals in audio files. The audio files are fed to the media editor for being associated to one or more of the further images in a synchronized manner with the content of at least one of the said images.

Image data may be captured by a camera 120 reproducing the ultrasound system or part of it, the patient or an anatomic district of a patient and at least one of the operators of the ultrasound system. The image data acquired by the camera is processed by a video processor 122 and also fed to the media editor for being combined in a multimedia representation with the audio files and/or with one or more of the acquired images and/or with the GUI images and/or with the images reproducing textual or alphanumeric coded data.

The media editor 124 may be configured by settings of the user and/or by factory pre-sets to combine the image information and the audio information according to various schemes generating a common multimedia file or the acquired images and/or the GUI images and/or the images reproducing textual or alphanumeric data, the one or more audio files are made available as separate media files which can be downloaded and displayed in parallel in different areas of the display of a client and in a synchronized manner at least for some of the said images and or audio files.

The multimedia files generated by the media editor are fed to a media streaming module 125 which can be accessed through a video and audio streaming unit 128 by a client connecting to a communication unit or port 129 of the ultrasound system.

The client is configured to execute a connection using a short-range communication protocol. The said one or more protocols may be selected from the following exemplary list comprising: Bluetooth, Wi-Fi, ZigBee, UWB, IR.

The media editor 124 may also be configured to render part of the visual and or acoustic information not available by covering the display areas where this information is printed on the display screen by a banner and by silencing the audio files or part of them.

According to an embodiment the multimedia files generated by the media editor 124 may be stored in a media file memory 133 and the access to the said file by means of the media streaming module 125 can be executed in real-time or at a later time in relation to the time of generation of the visual and/or acoustic information with an off-line streaming process.

The different units and processors 122, 123, 124, 125, 126, 128 may consist in all, or a part of them, in dedicated hardware.

In an alternative embodiment, said units and processors may consist, at least for a part of them, in a dedicated generic processing unit executing a software program in which the instructions are coded for configuring the generic processing unit in carrying out the functions of the specific processor and/or unit 122, 123, 124, 125, 126, 128.

In a further variant embodiment, at least part of said units and processors may consist in a software which is executed by the CPU 112 configuring said CPU and its peripherals for executing the functions of at least part of the units and processors 122, 123, 124, 125, 126, 128.

An active tag or a passive tag and or a marker or a combination thereof is secured to the probe. Said one or more tags or one or more markers are indicated schematically with the number 130 and are placed on the probe 101.

As it will appear more clearly in the following, said one or more tags or one or more markers can be detected by a corresponding detector of a tracking system. The detector recognizes said tag or markers and/or receives data from said tags or markers and generate position data in a predetermined reference system of said tags and/or markers. A processing unit of said tracking system is configured by a processing software to calculate the position coordinates of said tags or markers in said reference coordinate system and also to determine position and/or orientation of the probe 101 in the space defined by said coordinate system.

The sequencer/timing controller 110 may be programmed to manage acquisition timing which can be generalized as a sequence of firings. The sequence controller 110 manages operation of the TX/RX beamformer 103 and the A/D converter 104 and also send a synchronization signal to the tracking system for synchronizing the probe TX and RX firings with the data on the corresponding position and/or orientation in space of the probe when executing the said firings. This allows to store a data correlating univocally image data and probe position and orientation, this means the position and orientation in space, in the reference coordinate system of the slice or of a 3D-sector along which the image of a target body has been acquired.

Advantageously and preferably, also the position and orientation of the target body in relation to said reference coordinate system can be determined, for example by means of tags and/or markers and of detector of the position of the said tags or markers on the target body in relation to the reference coordinate system.

The acquired image data and the positional data of the probe may be used for several applications such as one or more of the applications disclosed above and particularly for generating three dimensional ultrasound images, for carrying out image fusion of a real time ultrasound image with a high resolution and or high detail three dimensional image acquired at an earlier time and/or with different imaging apparatus such as CT, MRI or PET or other systems and also for tracking the position of an interventional device in combination with ultrasound real time imaging of the region in which the interventional device is operating.

Figure 2:
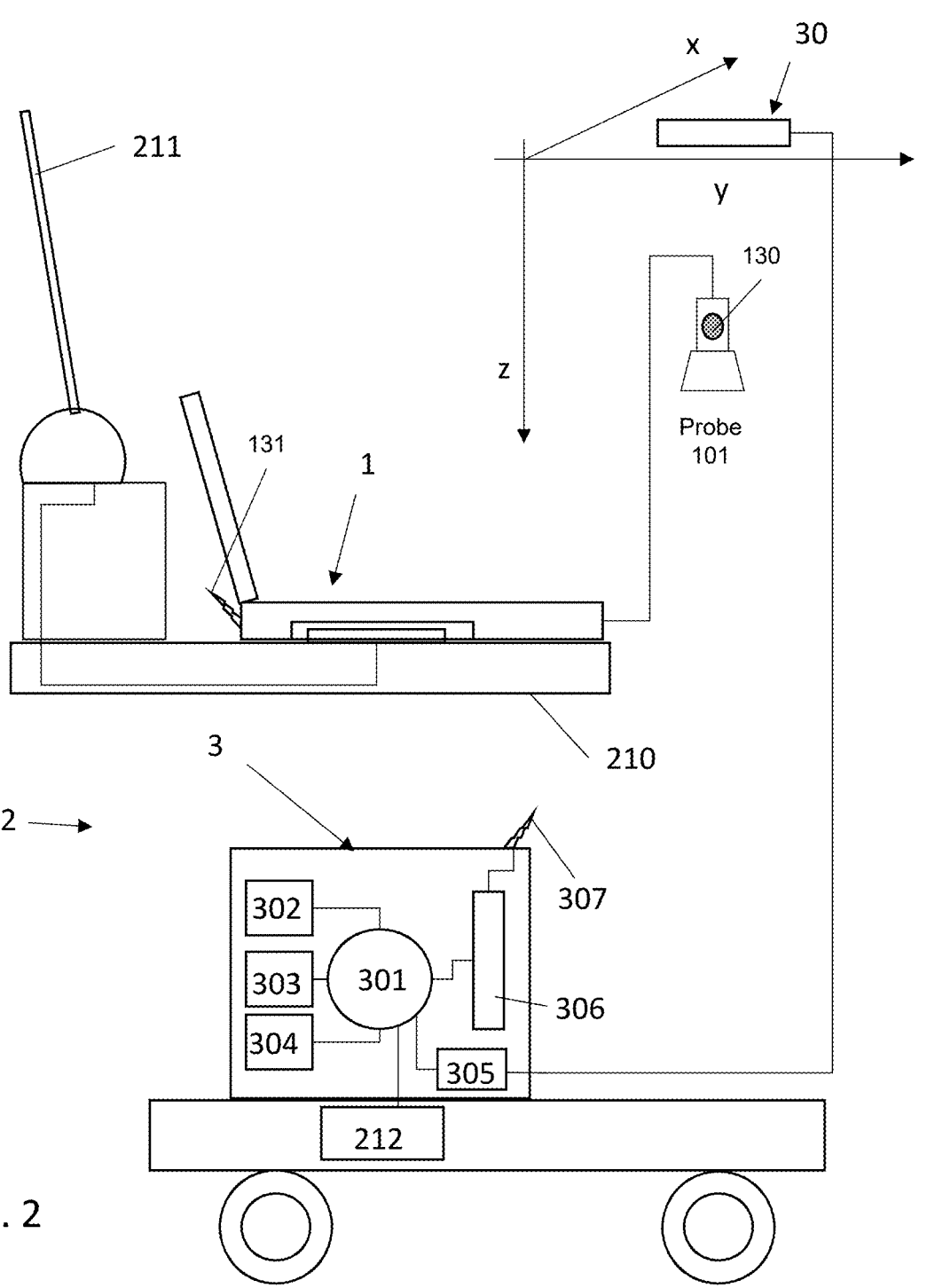
FIG. 2 shows a cart on which a tracking unit is mounted and on which an ultrasound imaging device can be secured to a support it, while a wireless communication and/or a wired connection ca be activated between the tracking and the ultrasound imaging device wearable and/or portable device according to embodiments herein.

FIG. 2 shows a cart comprising a tracking system which communicates wirelessly with an ultrasound imaging device 1, for example of the wearable or portable type, according to embodiments herein.

The cart 2 carries the processing unit 3 of the tracking system. A support table 210 may be configured in such a way that the ultrasound imaging device 1 can be releasably, mechanically secured to it. The cart 12 may further be provided with a display 211 that could be used as a second display of the ultrasound imaging device 1.

The probe 101 is provided with one or more tags and/or markers summarized schematically by the dot numbered with 130. A detector 30 scans a certain space in which also the target body is placed and detects the tag or tags and or the marker or markers 130 on the probe. The detection signals from the detector 30 are fed to a processing section 305 of the processing unit 3 of the tracking system. Here the signals from the detector are processed for extracting positional and/or orientation data of the probe 101 as it is displaced along the target body during an imaging session.

In FIG. 2, the reference coordinate system, in relation to which the data from the detector 30 provides position and/or orientation data of the probe, is indicated schematically by the coordinate system spanned by the vectors x, y and z.

As already disclosed with reference to FIG. 1, the ultrasound imaging device and the tracking system, and in particular the processing unit 3 of the tracking system need to exchange data for combining the image data acquired by the probe and the position and/or orientation which the probe had during the acquisition of said image data so that a clear position in space of the slice and/or of a 3D-sector acquired by the probe can be obtained with reference to the position and/or orientation of the target body.

The processing unit 3 and the ultrasound device 1 are provided both with a so-called short range communication unit indicated respectively with 129 in FIG. 1 and with 306 in FIG. 2. Antennas respectively 131 on the ultrasound device and 307 on the processing unit 3 provide for said wireless communication.

As already disclosed, different short range communication protocols may be used and can be present on the ultrasound device 1 and on the processing unit 3.

The processing unit 3 of the tracking system may be a generic processing hardware, having a memory in which a program is stored which, when executed by the said generic processing hardware, comprises the instructions for the processor to carry out the operating steps for processing the data provided by the detector and calculating the probe positional and/or orientation data.

As a non-limiting and non-exhaustive example, the processing unit 3 of the tracking system comprises a user interface for inputting data and/or commands and/or for selecting optional operations. Without any limiting intention, examples of said user interfaces may comprise, in any combination, one or more of the following devices: a display, such as, for example, the display 211, a keyboard, a mouse or similar pointing and selection devices, a microphone, a loudspeaker, a video or photo camera.

Some of the above interfaces may be integrated in a combination of a touch-screen display and a software controlling said touchscreen for carrying out the functions of different interface types, such as for example the functions of the display, of the keyboard and of the pointing and selection device.

A memory 303 is provided for saving the above disclosed software programs which comprises the instructions for carrying out the tracking functions.

As an optional feature, the processing unit 3 of the tracking system may be also configured to execute image processing tools on the image data and/or also on the positional and orientation data of the probe and thus of the image slices or space sectors acquired by it. This kind of processing tools may be selected by the user thanks to the input means 302 and launched by desire.

An electric power source, such as a rechargeable accumulator or battery 304, provides for energizing the processing unit 3 and, through it, also the ultrasound imaging device 1.

As it appears clearly from the above description, due to the fact that short range communication protocols operate also when the communicating devices are placed at a certain distance one from the other, is not necessary that, for carrying out probe tracking, the ultrasound imaging device 1 is placed on the cart 2.

This allows for example to carry out probe tracking during imaging of targets on patients which need to lie on a bed or to rest in specific positions, so that coming near to the patient with the cart is somehow difficult.

In relation to the technology for detecting the probe and determining its position and or orientation in space, many different techniques may be used. For example, and not limiting, one or more optical cameras cover a certain field of view and determine the position and or the orientation of the probe within the said field of view by carrying out image recognition processing of the image of the probe acquired by the said one or more cameras.

Alternatives thereto, the perturbations caused to a magnetic field by the probe may be used. Other alternatives are disclosed in the documents of the prior art cited above.

According to a possible variant embodiment, the support 210 for the ultrasound imaging device 1 and the ultrasound imaging device may be provided with mechanical connectors which secure the ultrasound imaging device 1 to the support 210 in a releasable way and/or separated connectors for generating an electric connection between lines outside the ultrasound imaging device 1 and inside it.

Said connectors can be separated one form the other or can be combined in order to generate at the same time a mechanical releasable connection and an electric releasable connection.

Figure 3:
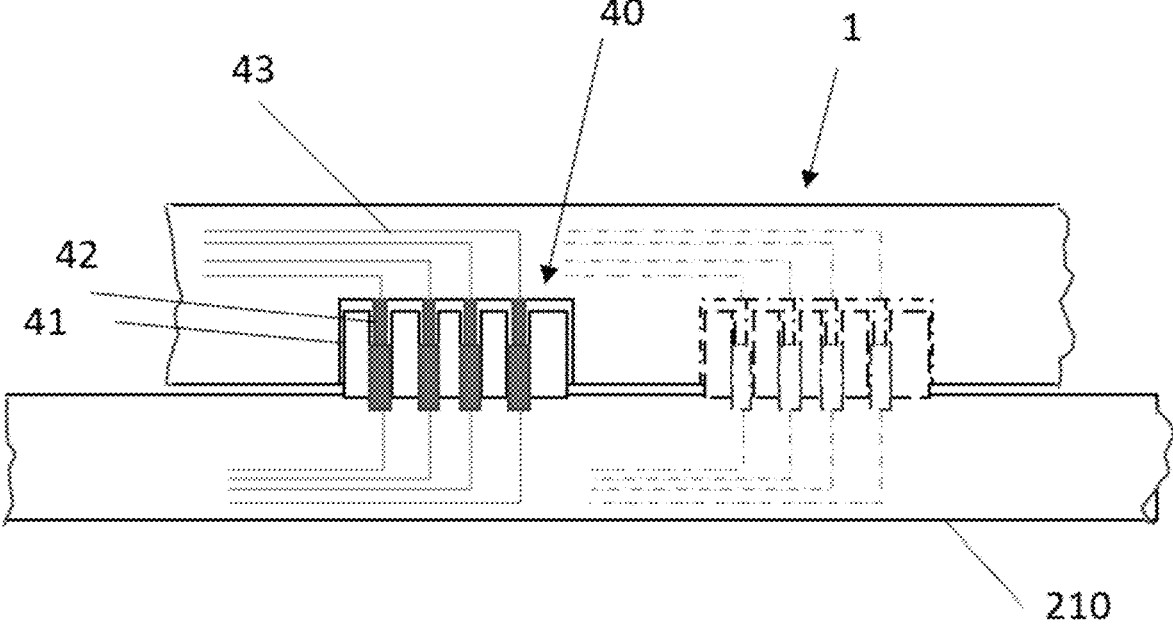
FIG. 3 shows a schematic sketch of possible releasable mechanical and also electric connectors between the ultrasound imaging device and the support on the cart.

An example thereof is shown schematically in FIG. 3. The example of FIG. 3 relates to a combined mechanical and electric connector assembly the case of the ultrasound imaging device 1 has one of the two connector elements of the connector assembly 40. This connector element comprises at least one slot 41 in which male contact electrodes 42 are positioned at a distance one from the other and from the peripheral walls of the slot 41. Further similar slots 41 can be provided on the case of the imaging device 1 as indicated by the one illustrated with discontinuous lines.

The electrodes 41 are male in this case, but could also have alternatively a female configuration. Each electrode 42 is connected to an electric conductor 43 leading to a certain operative section of the ultrasound imaging device electronics (here not shown in detail) and disclosed in the high-level diagram of FIG. 1. For example, one of the lines 43 could connect to the power supply 111, another to the sequence controller 110 or to the CPU 112 and further lines to other units such as for example a network communication unit operating by wired connection according to one or more of the previously disclosed network communication protocols.

The other connector element 44 is provided on the support 210 of the cart provided for the ultrasound imaging device 1 and comprises a male element which has a shape and dimensions corresponding to the one of the slot 41 so that a mechanical joint by friction can be obtained between the two connector elements 41 and 44.

The connector element 44 on the support 210 is provided with an electrode 45 which is placed in such geometrical relation to the peripheral sides of the connector element 44 that, when the connector element 44 is engaged in the connector element 41, each or at least some of the electrodes 45 come into contact with a corresponding electrode 42 of the connector element 40 thereby generating an electric conductive connection between said electrodes. Each electrode 45 is also connected to an electric conductor line 46. The lines 46 may be connected on the other side to different units of the processing unit 3 of the tracking system such as one or more memories, the processor 301, a communication unit operating by means of wired connection such as a network communication unit operating according to one or more of the above mentioned network communication protocols or other units.

Wired network communication between the tracking system and the ultrasound imaging device may be useful for enhancing the processing speed and/or for example in an environment in which a high number of wireless communication is carried out between several different devices.

Figure 4:
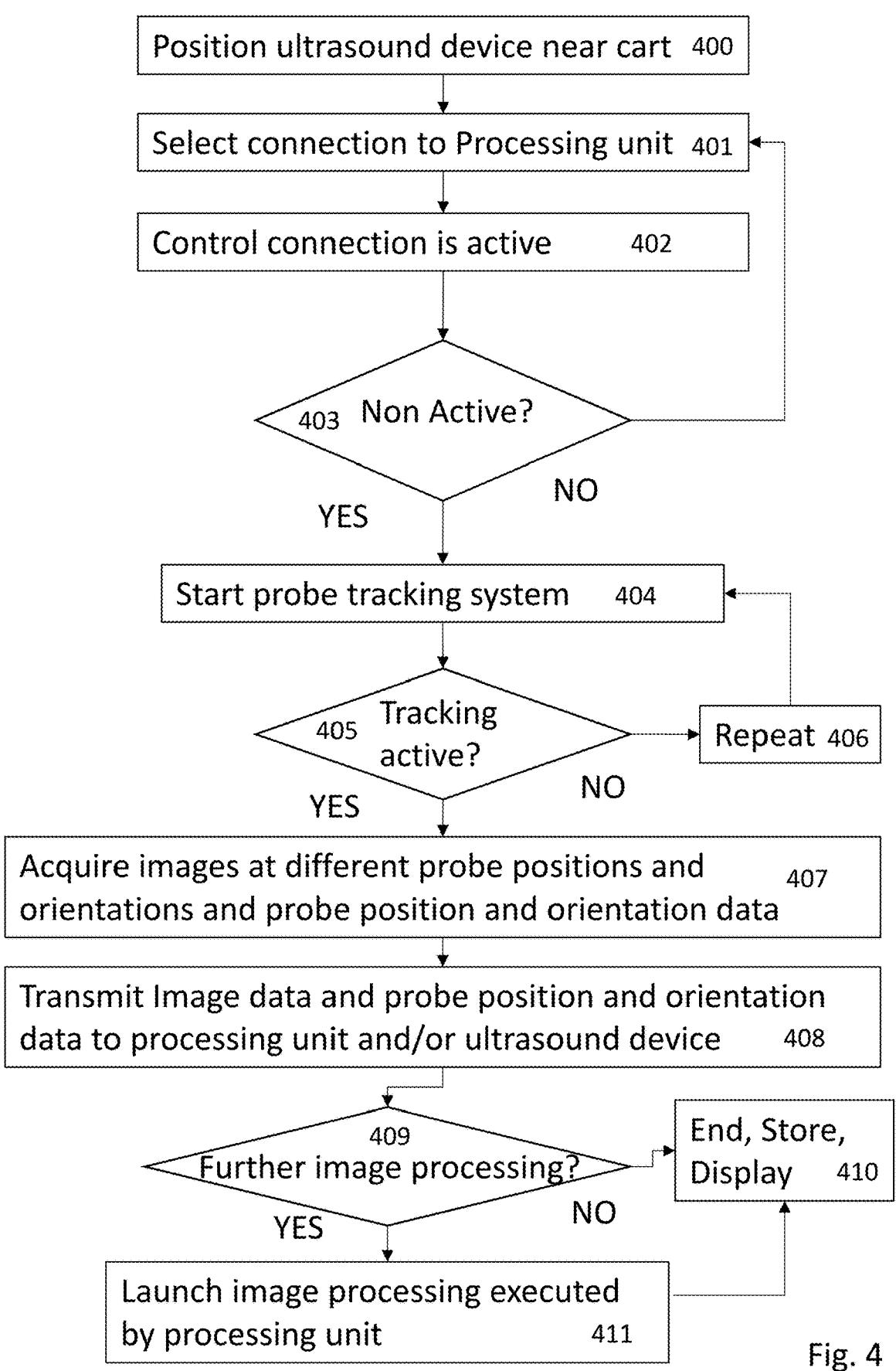
FIG. 4 shows a flow diagram of operating the ultrasound imaging device and the tracking system according to embodiments herein.

FIG. 4 shows a possible embodiment of the method for carrying out probe tracking processes with a system according to embodiments herein and particularly to the above disclosed embodiments.

Step 400 provides for positioning the ultrasound imaging device 1 near the cart 2, and not necessarily on the support 210 of the cart 2, either freely or in a secured manner to said support 210. The distance between cart 2 and ultrasound imaging device must be within the limits of the range for providing a communication link of the short-range communication system used by the ultrasound imaging device 1 and the cart 2 or the processing unit 3 of the tracking system.

At the ultrasound imaging device 1, the routine for selecting a connection to the processing unit 3 of the tracking device is carried out at 401. When several different communication units operating each one with a different short range communication protocol are present, the user might select also the kind of communication protocol to be used for connecting the imaging device 1 to the processing unit 3 of the tracking system.

Connection routine might request that steps have to be executed at the ultrasound imaging device 1 only, at the processing unit 3 of the tracking system only or at both imaging device 1 and processing unit 3 depending on the kind of communication protocol used.

At step 402 a control is carried out if the communication link is active and at step 403 if the communication link is not active the steps 401 and 402 for connecting the ultrasound imaging device 1 to the processing unit 3 of the tracking system and/or to the cart 2 are repeated.

If the communication link is active, then the ultrasound imaging device may be used for image acquisition and contemporary probe tracking in relation to its position and to its orientation as indicated by 404.

At step 405, a check can be carried out for verifying if the tracking of the probe is active and works properly. If not, the tracking system and ultrasound device setup has to be repeated as indicated by step 406.

If tracking works properly, the step 407 of acquiring ultrasound images and at the same time the positional data and the orientation data of the probe when acquiring a corresponding image are detected and then transmitted to the processing unit 3 and/or to the ultrasound imaging device 1 as indicated by 408. Here different processing steps of said image data and said positional and orientation data of the probe may be carried out such as simply univocally correlating said data and then saving said data or to provide said data to a further processing tool executed entirely and/or partially by the processing unit 3 of the tracking system and/or also entirely and/or partially by the ultrasound imaging device 1.

If further image processing is desired as indicated at step 409, a corresponding image processing tool can be launched for being executed entirely and/or partially by the processing unit 3 of the tracking system and/or also entirely and/or partially by the ultrasound imaging device 1. If not, the process is terminated as indicated at step 410 and the obtained data may be stored and/or displayed and or otherwise used.

It has to be noted that the communication unit 212 for the transmission and reception communication between the processing unit of the tracking system and the ultrasound imaging device may be resident on the cart as a separate and physically independent unit relatively to the ultrasound imaging device 1 and the tracking system, particularly the processing unit of the tracking system.

Said communication unit 212 may be connected to the processing unit 3 of the tracking system by means of a wired hardware connection to the said processing unit 3 of the tracking system so that it comes under the control of the processor 301 of the said processing unit 3 or it can operate as a sort of bridge or intermediate communication unit which connects wirelessly by means of a short range communication protocol with the processing unit 3 of the tracking system and with the ultrasound imaging device, so that different tracking systems and different ultrasound imaging devices also of different producers may be associated to a same cart without the need of being bounded to a specific ultrasound imaging device 1 and to a specific tracking system.

From the above disclosure, the advantages of the present disclosure appear clearly. No cost relating to the tracking system are added to the costs of the ultrasound imaging device. The provision of a probe tracking system does not have any impact on the device certification of the imaging device as the consequence of the integration of a tracking system in the ultrasound device and vice versa. The design of the ultrasound device is free form constraints due to the provision of the tracking system. Phase out devices do not extend to either the ultrasound device or the tracking system which may be substituted separately one from the other. Due to the wireless connection, the ultrasound device can be freely positioned in space in relation to the cart with the only limit to remain within the operating range of the short-range communication units. It is also possible to configure the trolley in such a way that it is compatible with different ultrasound devices and different tracking systems so to allow maximum flexibility in combining trolley, ultrasound device and tracking system.

The invention claimed is:

1. A system for acquiring ultrasound diagnostic images, comprising:
an ultrasound imaging device comprising:
a probe provided with one or more electroacoustic transducers;
a unit configured to transmit an ultrasonic beam through the transducers within a body under examination;
a unit receiving and processing ultrasound signals received from the one or more electroacoustic transducers for generating real-time images,
a probe tracking system comprising probe detecting sensors and a processing unit for calculating the probe position and/or orientation and/or displacement from data provided by the probe detecting sensors,
wherein at least the processing unit of the probe tracking system is a physically separated unit from the ultrasound imaging device and said ultrasound imaging device and said probe tracking system communicate by means of a short-range wireless communication protocol through a short-range wireless communication unit and/or a network communication unit that is stably provided on a cart and is configured to communicate at the same time with the ultrasound imaging device and with the probe tracking system, particularly its processing unit.

2. The system according to claim 1, wherein said short range communication protocol is selected from: Bluetooth, Wi-Fi, ZigBee, UWB, or IR.

3. The system according to claim 1 further comprising a cart, said cart being provided stably with the probe tracking system.

4. The system according to claim 3, wherein the cart comprises a support for the ultrasound imaging device, the support and the ultrasound imaging device being provided with cooperating releasable mutual fastening means.

5. The system according to claim 4, wherein with said mutual fastening means, or integrated in at least one or some of the said mutual fastening means of the ultrasound imaging device to the support on the cart, there are provided electric connectors for connecting at least one port of the ultrasound imaging device with a power source provided on the cart.

6. The system according to claim 1, wherein the ultrasound imaging device and/or the probe tracking system and/or the cart are provided with ports to be connected with a wired connection to a communication network including a communication network operating according to a known network protocol including a TCP/IP protocol.

7. The system according to claim 6, wherein each of the ports of the ultrasound imaging device and/or the probe tracking system and/or the cart is a RX/TX port of a communication interface.

8. The system according to claim 1, wherein the probe tracking system comprises:

a unit for registering an ultrasound image acquired in real-time by the ultrasound imaging device with a pre-acquired image and for registering a coordinate system of the body under examination, a coordinate system of the probe and a coordinate system of the pre-acquired image into a single coordinate system, and a unit for displaying a sequence of fusion images, each fusion image comprising the corresponding acquired real-time ultrasound image and image data of the pre-acquired image falling onto a same field of view and/or sector volume and/or slice of the ultrasound image acquired by the ultrasound image device.

9. The system according to claim 1, comprising a plurality of ultrasound imaging devices including the ultrasound imaging device, the plurality of ultrasound imaging devices communicating by means of the short-range wireless communication protocol with the probe tracking system hosted in the cart.

10. A method for acquiring ultrasound images of a target body through an ultrasound imaging device, the method comprising:

tracking position and/or orientation and/or displacement of a probe during image acquisition;

univocally associating the position and/or orientation and/or displacement of the probe to an image acquired with the probe in said position and/or orientation and/or during said displacement;

storing a combination of acquired image and data on the position and/or orientation and/or displacement of the probe during acquisition of the image;

wherein the tracking and the univocal association of the position and/or orientation and/or displacement of the probe and the storing in a memory are carried out by a tracking system which is a separate physical unit from the ultrasound imaging device, while the ultrasound imaging device and said separate physical unit communicate by means of a short-range wireless communication protocol and/or other wireless communication protocol;

wherein the ultrasound imaging device is removably secured to a common support structure of the tracking system and the ultrasound imaging device, the common support structure comprising a cart, a stand, or a trolley; and wherein the cart is provided with a separate and resident communication unit, said communication unit being configured to communicate with the ultrasound imaging device and with the tracking system forming a communication interface between the ultrasound imaging device and the tracking system each one provided with a communication unit;

said communication units being configured to operate according to the short-range wireless communication protocol.

* * * * *